United States Patent [19]
Anderson

[11] 3,975,290
[45] Aug. 17, 1976

[54] AEROSOL SYNTHESIS OF CERAMIC POWDERS

[75] Inventor: Richard C. Anderson, Chagrin Falls, Ohio

[73] Assignee: The United States of America as represented by the Secretary of the Navy, Washington, D.C.

[22] Filed: Nov. 20, 1973

[21] Appl. No.: 417,698

[52] U.S. Cl. .............................. 252/301.1 R; 106/65; 331/94.5 F; 331/94.5 T; 423/15; 423/252
[51] Int. Cl.² ..................... H01S 3/06; C01F 15/00; C01F 17/00
[58] Field of Search .............. 252/301.1 S, 301.1 R, 252/301.1 L; 423/15, 252; 75/108; 331/94.5 F, 94.5 T; 106/65

[56] References Cited
UNITED STATES PATENTS

| | | | |
|---|---|---|---|
| 2,849,286 | 8/1958 | Welt et al. | 423/21 |
| 3,214,238 | 10/1965 | Rombau et al. | 252/301.1 R |
| 3,393,055 | 7/1968 | Stevenson | 423/15 |
| 3,640,887 | 2/1972 | Anderson | 252/301.1 R |
| 3,790,492 | 2/1974 | Fulwyler | 252/301.1 S |
| 3,897,358 | 7/1975 | Greskovich et al. | 252/301.1 R |

OTHER PUBLICATIONS

Cotton, F. A. et al., Advanced Inorganic Chemistry Interscience Publishers, New York, 1972, pp. 1067 and 1095.

Greskovich, Co. et al. "Polycrystalline ceramic lasers," J. Appl. Phys. vol. 44, No. 10, Oct. 1973, pp. 4599–4606.

Greskovich, C. et al., "Fabrication of Transparent $ThO_2$–Doped $Y_2O_3$" Bull. Amer. Ceram. Soc. 52, 473–478 (1973).

*Primary Examiner*—Benjamin R. Padgett
*Assistant Examiner*—Deborah L. Kyle
*Attorney, Agent, or Firm*—R. S. Sciascia; Philip Schneider; Thomas McDonnell

[57] ABSTRACT

A method of coprecipitating a mixed oxalate to be used as a laser material in which one of the reactants is introduced as droplets formed by an aerosol into a bath containing the second reactant.

2 Claims, No Drawings

AEROSOL SYNTHESIS OF CERAMIC POWDERS

BACKGROUND OF THE INVENTION

Neodymium-doped glass and neodymium-doped yttrium aluminum garnet single crystals (YAG) are commonly used as laser materials. The invention relates to the co-precipitation of a ceramic to be used as a solid laser material having an emission line width between that of neodymium-doped glass and YAG. Such a material is suitable for generating high average power combined with high peak power.

Neodymium-doped yttrium oxide ceramic is attractive as a laser material because it is expected to yield a higher energy output than either Nd-doped YAG or glass. The use of $Nd^{+3}$ as a fluorescent center in laser hosts has a principal advantage of providing a low threshold of stimulated emission at $1.078\mu$ and places a premium on optical homogeneity and a low cavity loss. Numerous glass compositions and the crystal YAG are currently the most important host materials utilizing $Nd^{+3}$ fluorescence for laser action. Glass can be made in larger sizes with excellent optical homogeneity, and being amorphous, has the inherent properties of high energy storage capability (low gain) and low thermal conductivity. On the other hand, YAG crystals are expensive and limited in size by crystal growth considerations. They have a relatively high thermal conductivity and a low energy storage capability (high gain). For these reasons, glass is favored for high energy Q-switched pulses while YAG is best suited to C.W. applications. Using the conventional rod design, high average pulsed power cannot be produced with either host. Yttrium oxide ceramic, whose properties are intermediate between those of glass and YAG. has the potential for achieving a higher average pulsed power than either glass or YAG.

To be useful, though, as a laser material, it is best if the ceramic is pore free, transparent, free of light scattering inclusions and chemically homogeneous. Currently, however, processing of neodymium-doped yttrium ceramic materials may result in a product having occasional pores or other inhomogeneities.

Similarly, precipitation of yttrium oxide powder to produce laser material often results in a ceramic suffering from "orange peeling". Orange peeling is an optical undulation in the structure due to a refractive index variation. Its cause is not known. Standard techniques for the reaction of a Y — Th — Nd salt solution with oxalic acid to form the neodymium-doped yttrium oxide powder often result in a ceramic having orange peel.

SUMMARY OF THE INVENTION

Accordingly, the invention relates to the co-precipitation of yttrium oxide powder to form a ceramic that is pore free, transparent, free of light scattering inclusions and chemically homogeneous. More specifically, by reacting an aqueous solution of oxalic acid with droplets of a nitrate solution formed by an aerosol, an yttrium oxalate powder precipitate is formed which is chemically homogeneous and may be used to produce a ceramic which does not suffer from "orange peeling".

It is therefore an object of the invention to provide a process for the production of ceramic powder which may be used to make laser material.

Another object of the invention is to provide a novel method of precipitating out a mixed oxalate powder.

Still another object of the invention is to produce a laser material that is pore free, free of inclusions, chemically homogeneous and does not suffer from "orange peel".

Other objects, advantages and novel features of the invention will become apparent from the following detailed description of the invention.

DETAILED DESCRIPTION

Neodymium-doped yttrium ceramic powder is produced by reacting a Y — Th — Nd salt solution with an aqueous solution of oxalic acid. $Th^{+4}$ is added to inhibit grain growth and enhance vacancy diffusion along the grain boundaries resulting in elimination of pores during firing. This reaction results in a precipitate of yttrium oxalate powder. The surface solution is decanted off and the powder is then washed with deionized water. A neodymium-doped ceramic can then be produced by vacuum filtering and oven drying the precipitate at about 110°C, calcining at 800°C in air for a number of hours, and pressing the precipitate into a rod or disk shape at between 4K and 40Kpsi. The rod or disk is then sintered in dry $H_2$ at about 2100°C. The resultant rod is then useful as an active laser material.

According to the novel aspects of the invention a bath containing an aqueous solution of oxalic acid is provided. Droplets of a nitrate solution having the formula $Th_{0.1}Nd_{0.02}Y_{1.78}(NO_3)_{5.3}$ are formed by an aerosol and introduced into the bath at room temperature and 1 atmosphere pressure producing a precipitate according to the following reaction $Th_{0.1}Nd_{0.02}Y_{1.78}(NO_3)_{5.3}$ + $2.9H_2(C_2O_4) + H_2O \rightarrow Th_{0.1}Nd_{0.02}Y_{1.78}(C_2O_4)_{2.9} \cdot XH_2O$ + $5.8\ HNO_3$.

The nitrate solution is prepared by mixing appropriate units of $Th(NO_3)_4 \cdot 4H_2O$ with $Y(NO_3)_3 \cdot 6H_2O$ and $Nd(NO_3)_3 \cdot 6H_2O$.

The purpose of the aerosol is to form droplets of uniform size which in turn results in oxalate powder particles of uniform size. Powder size control is important in establishing powder flowability, compaction, sintering rates and pore formation, all of which are necessary for the achievement of pore free Yttralase ceramic. Further, the use of aerosol is a technique for maximizing the reactant surface area. Chemical homogeneity of the oxalate precipitate is limited not only by particle size but also by the total of unreacted salt solution surface which can be brought into contact with the reagent solution of oxalic acid. For this reason the use of an aerosol is important in maximizing the surface area reacted. Similarly, it is important to maximize the surface area of the reagent solution reacted. Rapid stirring or agitating of an excess amount of the oxalic acid solution is helpful in generating a fresh reagent surface against which the aerosol nitrate solution can be sprayed.

The size of the aerosol used is not critical as long as the droplet size is uniform. Droplets ranging in size from 10 to 75 microns are preferrable.

To further illustrate a preferred embodiment of the invention, the following example is presented.

Example

For a ceramic with the final composition
89 mol % $Y_2O_3$
1 mol % $Nd_2O_3$
10 mol % $ThO_2$
take
147.9 gms $Y(NO_3)_3 \cdot 6H_2O$ 1.89 gms Nd(NO$_3$)$_3$·6H$_2$O
11.9 gms Th(NO$_3$)$_4$·4H$_2$O
and dissolve in 150 ml distilled H$_2$O to achieve an 80% saturated solution. This nitrate solution is reacted with an oxalic acid solution prepared by adding 222.1 gms H$_2$C$_2$O$_4$ to 2700 ml distilled H$_2$O. This solution contains 4 times the amount of H$_2$C$_2$O$_4$ required to completely react with the nitrate solution. All ingredients should be at least 99.9% and preferably 99.99% pure.

The nitrate solution is formed into aerosol droplets by an aspiration technique wherein filtered air is forced through a glass tube and draws the nitrate solution from the tip of an inner glass tube which is axially coincident with the air flow tube. By this method an aerosol of the nitrate solution can be made whose droplet size is in the 10 to 75 micron size range.

The aerosol droplets are directed toward the surface of the oxalate solution. The surface of the oxalate solution is constantly renewed by agitating the oxalate solution by vigorous stirring, e.g., with a magnetic stirring rod.

By this means an oxalate precipitate is formed with the composition $$Th_{0.1}Nd_{0.02}Y_{1.78}(C_2O_4)_{2.9} \cdot XH_2O$$

whose particle size is in the 2 to 15 micron range.

When completed, the precipitate is left to settle overnight and then decanted. Then the precipitate is washed and decanted several times with distilled water. Finally, the suspension is vacuum filtered, and washed with distilled water until the wash water shows a neutral pH.

The filter cake is then oven dried at 110°C for 3 hours and calcined in an alumina crucible at 800°C for 4 hours to decompose the oxalate and provide an oxide powder.

This oxide powder is pressed at 38,000 psi to the desired shape and fired in a molybdenum resistor furnace in flowing H$_2$ on the following schedule:
3000°C per hour rate of temperature rise to 1500°C and hold for 1 hour.
2400°C per hour rate of temperature rise to 2100°C and hold for 2 hours.
Add H$_2$O vapor to furnace and cool at 4200°C per hour to room temperature.

This method of preparation yields transparent ceramic samples of small grain size which are essentially free from small pores and of excellent optical homogeneity.

It is obvious the conditions of preparation may be altered somewhat and may even be optimized somewhat to produce samples of the highest optical quality.

Thus, by introducing the nitrate solution as droplets formed from an aerosol, an yttrium oxide ceramic can be produced that is pore free, free of inclusions, chemically homogeneous and does not suffer from "orange peel".

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A method of co-precipitating a mixed oxalate which comprises providing a bath containing an aqueous solution of oxalic acid, forming droplets of a Th—Nd—Y salt solution from an aerosol spray and introducing said droplets into said bath while agitating said aqueous solution.

2. A method of co-precipitating a mixed oxalate which comprises providing a bath containing an aqueous solution of oxalic acid, forming droplets of Th$_{0.1}$Nd$_{0.02}$Y$_{1.78}$(NO$_3$)$_{5.3}$ from an aerosol spray and introducing said droplets into said bath while agitating said aqueous solution.

* * * * *